United States Patent [19]

Hsu et al.

[11] Patent Number: 5,290,703
[45] Date of Patent: Mar. 1, 1994

[54] METHOD FOR THE SEPARATION OF HIGH DENSITY LIPOPROTEIN FROM BLOOD SAMPLES

[75] Inventors: Chen-Jung Hsu, Chappaqua, N.Y.; Robert C. Payne, South Bend; James A. Profitt, Goshen, both of Ind.

[73] Assignee: Miles, Inc., Elkhart, Ind.

[21] Appl. No.: 990,592

[22] Filed: Dec. 14, 1992

[51] Int. Cl.$^5$ .................... G01N 33/92; G01N 33/49; G01N 1/18

[52] U.S. Cl. ..................... 436/71; 436/175; 436/177; 436/178; 436/527; 435/11; 210/782; 530/359; 530/411

[58] Field of Search .............. 530/359, 411; 435/11; 436/71, 177, 178, 175, 527; 210/782

[56] References Cited

U.S. PATENT DOCUMENTS

| | | | |
|---|---|---|---|
| 4,576,928 | 3/1986 | Tani et al. | 502/404 |
| 4,637,994 | 1/1987 | Tani et al. | 502/404 |
| 4,814,077 | 3/1989 | Furoyoshi et al. | 210/266 |
| 4,883,765 | 11/1989 | Tamir et al. | 436/71 |
| 4,923,439 | 5/1990 | Spidel et al. | 604/6 |
| 5,034,332 | 7/1991 | Rapacz et al. | 436/71 |
| 5,064,769 | 11/1991 | Gambert et al. | 436/516 |
| 5,118,613 | 6/1992 | McGowan | 435/11 |
| 5,141,872 | 8/1992 | Tamir | 436/71 |

OTHER PUBLICATIONS

"A Comprehensive Evaluation . . . Lipoprotein Cholesterol", Journal of Lipid Research, vol. 19, 1979 (Warnick et al.).

"Simultaneous Determination . . . with use of Heprin, $Ca^{2+}$ and Anion Exchange Resin", Noma et al. Clinical Chemistry, vol. 24, No. 9, 1978.

"Improved Method . . . in High-and-low Density Lipoproteins", Noma et al, Clinical Chemistry, vol. 25, No. 8, 1979.

"Separation and Quantitation . . . Precipitation Procedure", Gidez et al, Journal of Lipid Research, vol. 23 1982.

"Simplified Methods for Measuring Cholesterol . . . Serum Compared", Whitaker et al, Clinical Chemistry, vol. 32, No. 7, 1986.

Primary Examiner—James C. Housel
Assistant Examiner—N. Bhat
Attorney, Agent, or Firm—Jerome L. Jeffers

[57] ABSTRACT

A method for separating high density lipoproteins from blood serum or plasma. The method involves contacting the blood sample with an absorbant material comprising porous silica or silicate to adsorb the high density lipoprotein in preference to other lipoproteins in the blood sample. When combined with means for removing very low density lipoproteins and chylomicrons from the blood sample, the remaining low density lipoproteins can be measured directly.

15 Claims, 1 Drawing Sheet

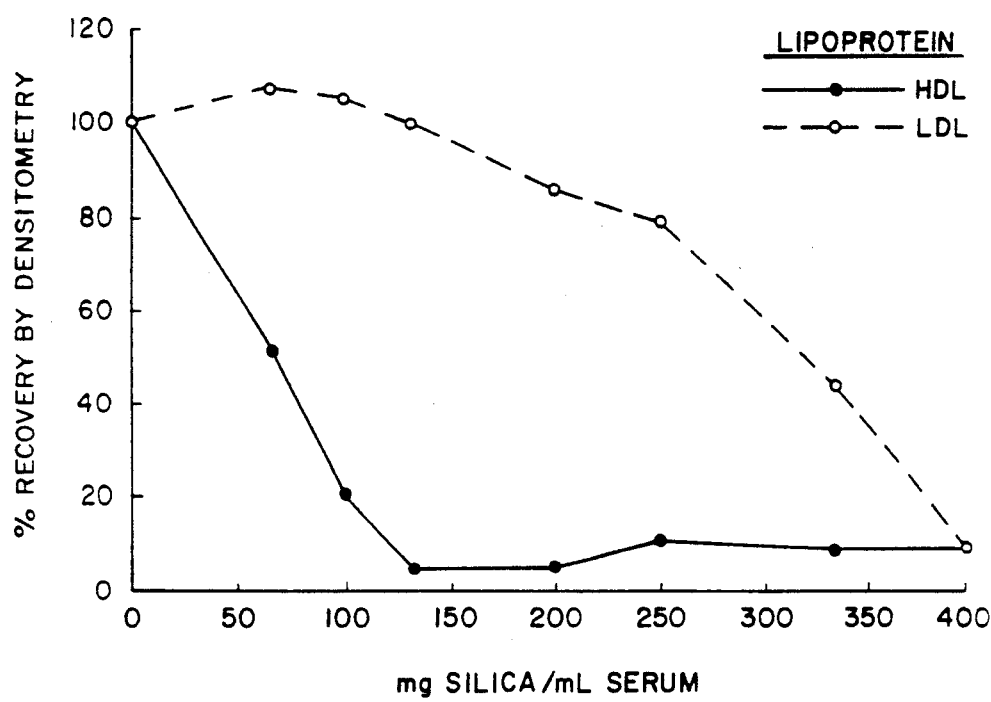

METHOD FOR THE SEPARATION OF HIGH DENSITY LIPOPROTEIN FROM BLOOD SAMPLES

BACKGROUND OF THE INVENTION

This invention is in the field of clinical assay techniques and involves the measurement of low density lipoprotein cholesterol.

Lipoproteins are complex particles comprising proteins and lipids which are found in the circulatory system. One of their functions is to carry water insoluble substances, such as cholesterol and cholesterol esters, for eventual cellular utilization. While all cells require cholesterol for growth, the excess accumulation of cholesterol by cells can lead to certain diseases including atherosclerosis. It is known that the amount of total serum cholesterol can be correlated with the incidence of atherosclerosis.

There are several classes of lipoproteins in serum, for the most part, classified by their density. These classes include very low density lipoprotein (VLDL), low density lipoprotein (LDL) and high density lipoprotein (HDL). All of these lipoproteins contain varying amounts of cholesterol. A total serum cholesterol determination is the sum of the amount that each lipoprotein contributes to the total lipoprotein population of the serum. This determination is further complicated by the presence of chylomicrons (cholesterol bearing precursors to lipoproteins) which can be present in the blood of individuals who have not fasted prior to having their blood drawn.

It has long been suspected that specific lipoprotein types were more closely associated with the progression of heart disease, including atherosclerosis, than others. More recent studies have implicated LDL as the class of lipoprotein responsible for the accumulation of cholesterol in the cells whereas HDL has been shown to be active in the removal of excess cholesterol from cells. Accordingly, various systems have been proposed for the measurement of cholesterol bearing lipoproteins in general and LDL in particular.

Amorphous silica, i.e. that form of $SiO_2$ which lacks a crystal structure, has been used as an adsorbant since at least as early as World War I when it was considered for use as an absorbant in gas masks. Amorphous silica is broadly divided into three categories: vitreous silica or glass made by fusing quartz; silica M made by irradiating either amorphous or crystalline silica with high speed neutrons and microporous silica and microparticulate silica. The microparticulate silicas include pyrogenic silicas and silicas precipitated from aqueous solution. Pyrogenic silicas are formed at high temperature by condensation by of $SiO_2$ from the vapor phase, or at lower temperature by chemical reaction in the vapor phase followed by condensation.

Silica formed in aqueous solution can occur as sols, gels or particles. A gel has a three-dimensional, continuous structure, whereas a sol is a stable dispersion of fine particles.

Silica gels are classified into three types. Regular density gel is made by gelling in an acid medium, which gives very small particles with high surface area (750–800 m$^2$/g). The average pore diameter is 22–26 Å, and the pore volume is 0.37–0.40 mL/g. Regular density gel contains about 6 wt% water as surface hydroxyl groups, which imparts a high propensity for adsorption of water and other polar molecules. Regular density gel exhibits a high selectivity for polar molecules and a large percentage of small pores. Intermediate density silica has a lower surface area (300–350 mg$^2$/g) but larger pore volume (0.5–1.1 mL/g). The average pore diameter is 120–160 Å and the particles are larger than those of regular density gel. Because of the large pore size, intermediate density gel has a large capacity for water absorption at high humidities. Low density silica gel has a lower surface area (<200 m$^2$/g), larger pore diameter (>180 Å) and a larger pore volume (>1.5 mL/g) than the other types. It is usually prepared as a very fine powder of extremely low density. When silica is used as an absorbent, the pore structure determines the gel adsorption capacity. Pores are characterized by specific surface area, specific pore volume (total volume of pores per gram of solid), average pore diameter, pore size distribution and the degree to which entrance to larger molecules is restricted by small pores. These parameters are derived from gas or vapor adsorption isotherms, mercury penetration studies, low angle X-ray scattering, electron microscopy, and gas permeability or measurement of the volume of imbibed liquid.

The most common way of preparing silica gel involves acidification of sodium silicate to a pH less than about 10. Silica can be gelled in spherical form by spray-drying, or by spraying droplets onto an immiscible liquid.

Microporous silica gels are obtained by heating a hydrated gel at 1000° C. for about 10 hours. Siliceous materials can be made with extremely small pores such as is the case with impervious silica, porous glass and silica used as an adsorbent for certain specific materials which are determined by the surface composition and pore size of the silica gel. The present invention is concerned with the use of large pore silicas and silicates such as microporous silica, silica gel and controlled pore glass as selective adsorbant materials for HDL from blood serum or plasma.

Precipitated silica (also called particulate silica) is composed of aggregates of ultimate particles of colloidal size that have not become linked in a massive gel network. Precipitated silicas are either formed from the vapor phase (fumed or pyrogenic silicas) or by precipitation from solution. In the preparation of pyrogenic or fumed silica, sand is vaporized at about 2000° C. On cooling, anhydrous amorphous silica powders form in the presence of a reducing agent such as coke. The amorphous silica sublimes at about 1500° C. to provide Si which is then oxidized to produce particulate $SiO_2$. Pyrogenic or fumed silica is typically used as a thixotropic agent in polyester-glass reinforced plastics; as a reducing and thickening agent in rubber, plastics, silicone and epoxy resins as well as a thickening and gelling agent.

Pure silica is composed of the elements silicon and oxygen. Materials are still referred to as "silicas" after metals, metal oxides or metal salts are added; e.g. flint is a silica with added iron oxide. Glass has a defined composition between $(K,Na)_2O$, $(Ca,Pb)O$, $6SiO_2$ and $5(K,Na)_2O$, $7(Ca,Pb)O$ and $36SiO_2$ with a general formula of $(K,Na)O \cdot Si_nO_{2n-1}(CaPb)O \cdot Si_nO_{2n-1} \cdot O(K,Na)$. While all silica based glasses can be called silicas, not all silicas are glass. The HDL adsorbant materials useful in the present invention are porous silica or silicates as the terms are used in their broadest sense.

U.S. Pat. No. 5,141,872 discloses the use of fumed silica for the selective adsorption of lipoproteins from plasma. The patentees point out that this procedure was known before their invention but claim the improvement of selectively desorbing HDL from the fumed silica by incubating with a detergent containing formulation. The commercially available fumed silica such as Cab-O-Sil from Cabot Company and Aerosol from Degussa are mentioned as being useful in this procedure.

The diameter of the LDL particle and VLDL particle are estimated at 220–250 Å and 300–800 Å respectively with chylomicrons being larger. Since the dimensions of a fumed silica such as Aersol 380 are less than about 70 Å and the HDL particle is estimated at 100 to 150 Å in diameter it can be concluded that this binding of lipoproteins as disclosed in U.S. Pat. No. 5,141,872 is based solely on non-specific surface adsorption. Particle size exclusion of the relatively larger lipoprotein particles is not a factor in that method since LDL and VLDL particles are too large to fit in any pores which may exist in the 70 Å silica particles. This technique achieves its selectivity by desorption in a separate step. The present invention involves the selective adsorption of the smaller HDL particles by the silica gel which, when combined with a mechanism for the separation of VLDL and chylomicrons, provides a fluid sample which can be analyzed for the remaining LDL without further treatment.

SUMMARY OF THE INVENTION

The present invention involves a method for separating high density lipoprotein (HDL) from a blood sample which comprises contacting said sample with finely divided, porous silica or silicate particles as absorbant for the HDL, said absorbant particles having surface pores of from about 80 Å to 500 Å in diameter to form adsorbant particle/HDL complex and separating said complex from the blood sample by solid/liquid separatory techniques to provide a blood sample substantially free of HDL. Preferred adsorbant materials include microporous silica, silica gel or controlled pore glass.

By combining this highly selective method of separating HDL from the blood sample with means for selectively removing VLDL and chylomicrons, the blood sample can be analyzed directly for its LDL concentration.

BRIEF DESCRIPTION OF THE DRAWING

FIG. 1 graphically represents Vydac 101TP silica mg usage/mL serum and selective lipoprotein recovery.

DESCRIPTION OF THE INVENTION

In the practice of the present invention, silica gel having a selective pore size is employed to specifically adsorb HDL present in the blood sample. Various means for separating VLDL and chylomicrons from the sample can be employed, such as for example by the use of a polyanion and divalent cation. We prefer to accomplish this removal by contacting the blood sample with a polyanion and a divalent cation, e.g. heparin and $MnCl_2$, in either the liquid or solid phase.

The present invention has application in medical diagnostics in situations where it is desirable to remove the HDL component from a mixture of lipoproteins in plasma or serum. Examples of such a situation include using the technique as a component of a system where other lipoproteins are also removed to thereby leave only a single lipoprotein which can be directly measured by a cholesterol content assay. Combination of this system with means for removing chylomicrons and very low density lipoprotein (VLDL) would result in a direct assay for low density lipoprotein (LDL), which is the lipid of greatest interest.

Alternatively, subtraction of the value for cholesterol in a blood sample, treated as suggested herein, from the value of total cholesterol in the original sample would allow one to deduce the amount of cholesterol carried by HDL in the sample.

In another application, the invention can be used as a means of dispensing lipoprotein interactive reagents in small, precise quantities, particularly where the silica reagent would be used in a subsequent procedure requiring the removal of particular lipoproteins from serum or plasma. For ease of the manufacture of medical diagnostic devices, the lipoprotein interactive reagents could be evenly distributed in a dry sheet. By cutting out a well defined area of the sheet, an accurate quantity of the active reagents would be at hand for convenient transfer to the desired container or location. In its simplest form the present invention involves a liquid system for selectively removing HDL from a blood sample which is preferably combined with one or more techniques for removing VLDL and chylomicrons from the sample to provide such a sample in which LDL can be directly measured.

In practicing the present invention, silica or silicate of the type previously described, the polyanion and soluble salt of a divalent cation are predispersed with water or other suitable solvent in a suitable vessel to which blood, in the form of serum or plasma, is added. After mixing and incubation at room temperature for several minutes, the silica and flocculated (floating) VLDL-chylomicron/polyanion-divalent cation complex is removed from the mixture by solid-liquid separatory techniques such as centrifugation or filtration through a filter having pores smaller than the silica particle diameter, for example, through a filter of approximately 2 micron pore size. Alternatively, the infranate can be sampled by pipette. The filtrate or a portion of the centrifugal infranate is sampled for cholesterol concentration by conventional serum total cholesterol assay reagents, such as for example the cholesterol oxidase method as disclosed in Technicon Method No. SM4-2139F90, June 1990, a Technicon® AXON™ method sheet for the use of Technicon cholesterol reagents on the Technicon® AXON™ system. The value reported represents the cholesterol carried by LDL, which is of primary interest.

In a convenient embodiment of the present invention, HDL, VLDL and chylomicrons are separated from the serum or plasma by combining it with the porous silica or silicate, i.e. the porous siliceous material, divalent cation and polyvalent anion in a compressible chamber having at least one opening in the upper side thereof. This opening is covered by a filter, which is detachable or replaceable with a seal or cap, whose pores are of a size which will retain complexes of the porous siliceous particles and the adsorbed high density lipoprotein from the blood sample. Likewise, the pores should be small enough to retain substantially all of the complex formed by the interaction of VLDL/chylomicrons and with the divalent cation and polyvalent anion. Upon mixing and incubation, the HDL and VLDL/chylomicrons form complexes with the siliceous material and divalent cation/polyvalent anion respectively which are retained by the filter element. Thus, by compressing the chamber such as, for example, by squeezing it or using a piston type mechanism, the blood sample, bearing only its residual LDL is extruded through the pores in the filter. Typically, the pore size will range from 1 to 10 μ in diameter with a range of from 1 to 2 μ being preferred.

Suitable filter materials include porous plastic or glass fiber. Common filter devices contain additives such as detergents, fluid flow enhancers and agents to reduce binding to the filter material. These additives can alter lipoproteins, as shown by agarose gel electro-phoretic profiles. Where there is a need for the LDL lipoprotein to be delivered in its native state, a filter material devoid of added detergent or flow enhancers is preferred. For total cholesterol analysis systems, the effect of small amounts of leached filter additives is not a problem since only the cholesterol contained in the LDL fraction of the system will pass through the filter.

In practicing the present invention, the siliceous adsorbant is typically employed in an amount of from about 50 to 350 mg/mL of blood (in the form of plasma or serum) being tested; an amount of siliceous material ranging from 80 to 250 mg/mL is preferred. Selective removal of HDL is most efficient for 4 μ particle size VYDAC 101TP from The Separations Group, Hesperia, Calif., in the 80 to 250 mg/mL range. Crossfield Sorbsil C500 silica is similar but favors a range of 90 to about 300 mg/mL. Less silica fails to remove more than about 2/3 of the HDL whereas more silica has been observed to remove more than ⅓ of the LDL. As demonstrated by FIG. 1, the ideal amount of Vydac silica for HDL isolation is 133 mg/mL. The optimum silica concentration for LDL assay is influenced by other factors such as completeness of mixing or the presence of complexing reagents (heparin and manganese ion). Various amounts of silica (VYDAC 101TP) were studied using 5 fresh sera samples across the LDL range. Based on correlation with Friedewald reference methods, the correlation slope was closest to 1.0 with 80 mg silica/mL serum and the lowest correlation intercept was with 111 mg/mL. Within this range, we chose the minimum of the rootmean-square bias from the reference Friedewald method across the five samples; this is 91 mg/mL.

The porous silicas and silicates, also referred to as controlled pore glasses, preferred for use in the present invention are those three-dimensional, continuous structures of low density with a surface area of greater than 200 m$^2$/g. Particle size can range from 1 to 1000 μ in the longest dimension with a range of from 2 to 500 μ being preferred. The pore size normally ranges from about 80 Å up to about 1000 Å (preferably from 300 Å to 500 Å) in diameter with the pore volumes being greater than 1.5 mL/g.

The porous silicas and silicates which are useful in the present invention due to their ability to abstract HDL are those which have a substantial number of pores with sizes larger than the HDL particles. Preferably the average pore size of the particle's pore size distribution is greater than the HDL particle diameter. The siliceous adsorbant particles which are suitable for selectively adsorbing HDL in preference to LDL have an upper limit of pore sizes which has been found experimentally to correspond to porous material with pore diameters up to about 500 Å. The lower limit of pore size which exhibits selectivity for HDL in preference to LDL was 66–88 Å as exhibited by 5 μ Whatman Partisil 5 porous silica gel. At the extremes, the source of the porous siliceous material appears to be significant. While the Whatman Partisil 5 material exhibits some selectivity for HDL at a stated pore size of 66–88 Å, Sigma controlled pore glass at a stated pore size of 79 Å was not selective. The manufacturer's methods of determining pore size may not correspond to the apparent pore sizes under the conditions which the silicas or silicates are used in the present invention. The optimum pore size seems to be about 300 Å as determined by the methods of the manufacturers. A preferred range is about 200 Å to 350 Å as the most useful silica or silicate examples among all manufacturers fall in this range.

By employing means to remove VLDL and chylomicrons from the blood sample in addition to the removal of HDL by the particulate absorbant material, there will remain only LDL in which the cholesterol concentration can be directly determined. The use of a polyvalent anion/divalent cation is a preferred means for removal of VLDL and chylomicrons. The divalent cation, typically in the form of $MnCl_2$ or $MgCl_2$, and polyvalent anion, typically heparin or dextran sulfate. Their most useful concentrations are interdependent with a final concentration of from about 25 to 500 millimoles per liter divalent cation and from 0.05 to 0.15 grams per liter polyvalent anion being useful.

In the presence of Vydac Silica at 111 mg/mL serum and porcine heparin at 0.05 g/L the most useful range of divalent cation found was 50 to 100 mM $MnCl_2$ whereas in the presence of Vydac Silica at 111 mg/ml serum and porcine heparin at 0.10 g/L, the useful range of divalent cation was 200 to 467 mM $MnCl_2$.

This method of separating lipoproteins from blood in the liquid phase is further described in U.S. Pat. No. 4,746,605 the disclosure of which is incorporated herein by reference. In the technique disclosed in this patent, HDL is removed from the blood sample by precipitation involving the use of high density lipoprotein specific antibodies.

The practice of the present invention is further illustrated by the following examples:

EXAMPLE I

To 11.1 mg silica (Vydac Silica, 4 μ particle size, 300 Å pore size) in a 500 μl Eppendorf polypropylene tube was added 50 μl of 300 mM aqueous $MnCl_2$ (Sigma M-3634) with 0.15 mg/ml heparin (porcine H-3125 from Sigma) with subsequent mixing. A 100 μl portion of serum was added to provide a volume ratio of serum to reagent of 2:1 thereby providing a final concentration of 100 mM $MnCl_2$ and the combination was vortexed 5 times over a period of 15 minutes whereupon it was centrifuged for 10 minutes at 12,000×g. The infranate was separated from the precipitated solids and analyzed using the COBAS FARA (Roche) total cholesterol assay. The value reported by the standard total cholesterol assay was multiplied by the dilution factor of 1.5 to adjust for the dilution by the aqueous heparin-manganous chloride solution or 1.458 in the present case to further adjust for the small amount of water lost to the silica gel. Reference analysis of the original sera, i.e. COBAS FARA Total Cholesterol, COBAS FARA HDL cholesterol, COBAS FARA triglycerides and Paragon Lipogel, electrophoresis, NWLRC (Northwest Lipid Research Center) Friedewald cholesterol were carried out.

The removal of HDL from the blood sample by the present technique is suitable for use with various systems capable of running total and HDL cholesterol assays. This system compares well with the Friedewald and Technicon RA-XT method is indicated in the following example.

EXAMPLE II

Serum was added to a slurry of MnCl₂, porcine heparin in the ratio of 2 parts serum to 1 part $MnCl_2$-heparin solution to 111.1 mg silica Vydac 101TPB4/mL serum. The treated serum sample was mixed by vortexing and allowed to stand at room temperature for approximately 12 minutes before centrifuging at 12,000 ×g for 3 minutes. The total cholesterol of the infranate was determined on a Roche Cobas Fara clinical analyzer. The LDL-cholesterol values were obtained by multiplying the infranate total cholesterol by 1.5. Friedewald LDL-cholesterol values were calculated from independent determinations of total cholesterol, HDL-cholesterol and triglycerides according to the formula:

$$LDL\ Chol. = Total\ Chol. - HDL\ Chol. - \frac{Triglycerides}{5}$$

Values obtained using the method of the present invention (direct LDL cholesterol) are compared with those values determined by the Friedewald method. The correlation coefficient between the present method and the Friedewald method was 0.98 as can be determined from Table I.

TABLE I

| Sample Number | Direct LDL Cholesterol (mg/dl) | Friedewald LDL Cholesterol (mg/dL) |
| --- | --- | --- |
| 1 | 177 | 178 |
| 2 | 228 | 232 |
| 3 | 54 | 63 |
| 4 | 92 | 85 |
| 5 | 105 | 121 |
| 6 | 140 | 148 |
| 7 | 145 | 146 |
| 8 | 90 | 115 |
| 9 | 94 | 104 |
| 10 | 101 | 114 |
| 11 | 172 | 182 |
| 12 | 149 | 167 |

EXAMPLE III

Serum (220 μL) was added to 110 μL of aqueous solution containing 0.3M MnCl₂ and 0.15 mg/ml porcine heparin and 20 mg Vydac 101 in a plastic Porex SQEASY reservoir. The reservoir was capped, briefly mixed and allowed to stand at room temperature for approximately 12 minutes. A filtration cap equipped with a Porex UF 2 micron filter was placed on the reservoir and its fluid contents were forced through the filter by squeezing the reservoir. In this manner, a filtrate was obtained which contained the unassociated LDL, while the HDL associated with the silica gel and VLDL/chylomicrons associated with the MnCl₂/heparin were effectively removed by the 2 micron filter. This was evidenced by optical density of lipoprotein bands from agarose gel electrophoresis which revealed no loss of LDL in the filtrate and that the ratio of HDL to LDL changed from 1:2 before treatment to 1:21 after treatment.

EXAMPLE IV

Selective Removal of HDL From Serum by Microporous Silica

To 1.5 mL plastic microcentrifuge vials containing (1) microporous silica [VYDAC 101TP; 270–320 Å, average 300 Å pore size from The Separations Group, Hesperia, Calif.], (2) controlled pore glass [330 Å pore, PG 350-200, Sigma Chemical Co.], (3) controlled pore glass [79 Å pore, PG 75-200]or (4) amorphous fumed silica (non-porous CAB-O-SIL, Grade M5, 2 μ aggregates, Cabot Corp.) was added approximately 300 μL of fresh human serum. A fifth vial containing no silica was used as a control. The contents of the vials are summarized in Table 1.

TABLE 1

|  | Control | Controlled Pore Glass | | Microporous Silica | Fumed Silica | |
| --- | --- | --- | --- | --- | --- | --- |
|  |  | C P G-80 | PG 350-200 | Vydac | Cab-O-Sil | Cab-O-Sil |
| mg/mL | 0 | 111 | 111 | 111 | 11 | 55 |
| mg solid | 0 | 30.5 | 33.6 | 35.1 | 4.4 | 17.0 |
| μL serum | 300 | 275 | 303 | 316 | 396 | 309 |

Each tube was capped, briefly vortexed, placed in a larger cylindrical tube and simultaneously placed on a rolling hematology mixer (Fisher Scientific) for 15 minutes. The vials were then centrifuged for 8 minutes at 14,000×g. Approximately 225 μL of clear supernatant fluid was transferred from each vial to a new vial, capped and vortex mixed. The infranate samples and the original human serum were analyzed by agarose gel (Beckman Lipogel) electrophoresis (Beckman Paragon System), lipid staining and optical densitometry (Beckman Appraise). Comparison of treated serum results to untreated serum indicated preferential removal of HDL over that of LDL or VLDL by the microporous silicas (Vydac) and the 330 Å controlled pore glass. There was observed no useful selectivity for HDL by the fumed silica or PG 75-200 controlled pore glass. In this experiment, absorbance units were obtained using the Beckman Appraise Densitometer for each 0.1 mm of the scan of each electrophoresis gel lane. Absorbance at 600 nm was normalized to that of the Hewlett Packard 8452A Spectrophotometer by dividing the raw appraise absorbance data by a factor of 2200. This factor was arrived at by comparison of the response to a blue transparent film standard on each instrument. The absorbance values were converted to % recovery of lipoproteins by the formula 100%×[absorbance X width (mm) of the experimental lipoprotein band]/[absorbance ×width (mm) of the control lipoprotein band]. The control serum was a 2:1 dilution of human serum:water. The results of this experiment, both in terms of absorbance and % recovery of lipoproteins are set out in Tables 2 and 3:

TABLE 2

| | | Optical Densitometry of Lipoprotein Bands From Agarose Gel Electrophoresis (Absorbance X mm Units) | | | | |
|---|---|---|---|---|---|---|
| | | Controlled Pore Glass | | Microporous Silica | Fumed Silica Cab-O-Sil | |
| Lipoprotein | Control | PG 75-200 (79 Å Pores) | PG 350-200 (330 Å Pores) | Vydac | @ 11 mg/mL | 55 mg/mL |
| Chylomicrons | 0.05 | 0.04 | 0.05 | 0.05 | 0.06 | 0.06 |
| HDL | 1.27 | 1.39 | 0.09 | 0.15 | 0.75 | 0.04 |
| VLDL | 0.23 | 0.30 | 0.27 | 0.30 | 0.27 | 0.05 |
| LDL | 1.63 | 1.79 | 1.79 | 1.82 | 1.06 | 0.06 |

For controlled pore glass used at 111 mg/mL, the calculated recovery of HDL and LDL was 109% and 110% respectively for the 79 Å pore material and 7% and 100% respectively for the 330 Å pore material. The microporous silica, VYDAC 101TP, recovered HDL/LDL at 12%/112% when used at 111 mg/mL. Previous experience with fumed silica suggested that lipoprotein removal by 111 mg/mL silica is so complete that no information on selectivity can be gained by electrophoresis of the treated serum. Accordingly, more appropriate amounts of Cab-O-Sil were used. At 55 mg/mL the percent recovery of HDL/LDL was 3%/4% respectively. At a lower level (11 mg Cab-O-Sil/mL serum) the percent recovery HDL/LDL was 59%/65% respectively. Accordingly, it can be seen that while fumed silica removes HDL from serum, it exhibits no useful preference for abstraction of HDL over LDL. The quantity of chylomicron lipoprotein in the original sample was too small to allow a reliable percent recovery number to be calculated.

TABLE 3

| | | Optical Densitometry of Lipoprotein Bands From Agarose Gel Electrophoresis (% Recovery of Lipoproteins) | | | | |
|---|---|---|---|---|---|---|
| | | Controlled Pore Glass | | Microporous Silica | Fumed Silica Cab-O-Sil | |
| Lipoprotein | Control | PG 75-200 (79 Å Pores) | PG 350-200 (330 Å Pores) | Vydac | @ 11 mg/mL | 55 mg/mL |
| Chylomicrons | | | | | | |
| HDL | | 109 | 7 | 12 | 65 | 4 |
| VLDL | | 128 | 114 | 129 | 116 | 21 |
| LDL | | 110 | 110 | 112 | 59 | 3 |

EXAMPLE V

Fasting vs. Non-Fasting Direct LDL Cholesterol and Chylomicrons

Fresh serum was drawn twice from five subjects, once under fasting conditions and later in the same day 1.5 hours after a meal (postprandial). Four of the subjects developed sufficient postprandial chylomicron quantities to allow a percent recovery calculation on chylomicrons after reagent treatment. Quantities of chylomicrons were reduced to background levels by the method of the present invention. Direct LDL cholesterol measurement was only slightly affected by the postprandial condition being within 3 mg/dL+2% of the fasting value as illustrated by the following experimental section.

To plastic centrifuge vials containing a slurry of 20 mg Vydac 101TP 4 μ silica and 100 μL of a solution of 300 mM $MnCl_2$ and 26.7 U/mL (0.15 mg/mL) porcine heparin were added 200 μL of serum (111 mg silica/mL serum). The vials were vortex mixed five times over 15 minutes then were centrifuged at 14,000×g for 10 minutes. Portions of the infranates were compared to 2:1 serum:water dilutions of the original sera by agarose electrophoresis (Beckman Lipogel) on the Beckman Paragon System followed by densitometry (Beckman Appraise). The infranates were evaluated for Friedewald LDL cholesterol by the Northwest Lipid Research Center. The results are set out in Table 4.

TABLE 4

| Serum | Friedewald LDL-C NWLRC | Direct LDL-C |
|---|---|---|
| "A" Fasting | 166 | 155 |
| "F" Fasting | 32 | 29 |
| "G" Fasting | 99 | 90 |
| "I" Fasting | 111 | 106 |
| "S" Fasting | 254 | 224 |
| "A" Postprandial | 171 | 162 |
| "F" Postprandial | 19 | 30 |
| "G" Postprandial | 100 | 100 |
| "I" Postprandial | 101 | 110 |
| "S" Postprandial | 243 | 231 |

The correlation of postprandial, direct LDL cholesterol to fasting, direct LDL cholesterol was of slope = 1.02 and intercept −3.17 mg cholesterol/dL serum.

Electrophoretic profiles of subject sera were compared with and without treatment with the reagents of the present invention. Sera in which there were significant postprandial chylomicrons showed a reduction of the chylomicrons to background levels upon treatment with the LDL isolation reagents. Serum "A" developed the lowest level of chylomicrons and was deleted from Table 5 because it also included a significant, unresolved intermediate peak between LDL and VLDL.

TABLE 5

| | Optical Densitometry of Agarose Gels (AU-mm integration at 600 nm) Postprandial Sera With or Without Treatment With the LDL Isolation Reagents | | | |
|---|---|---|---|---|
| | Chylomicrons | LDL | VLDL | HDL |
| "F" Postprandial Control | 0.26 | 0.84 | 1.13 | 0.79 |
| "G" Postprandial | 0.11 | 1.20 | 1.32 | 0.84 |
| "I" Postprandial | 0.15 | 1.50 | 1.73 | 0.65 |
| "S" Postprandial | 0.14 | 2.42 | 0.98 | 0.64 |
| "F" Postprandial After Treatment | 0.03 | 0.44 | 0.04 | 0.04 |

TABLE 5-continued

Optical Densitometry of Agarose Gels
(AU-mm integration at 600 nm) Postprandial
Sera With or Without Treatment With
the LDL Isolation Reagents

|  | Chylomicrons | LDL | VLDL | HDL |
|---|---|---|---|---|
| "G" Postprandial | 0.03 | 1.08 | 0.23 | 0.04 |
| "I" Postprandial | 0.03 | 1.31 | 0.38 | 0.02 |
| "S" Postprandial | 0.03 | 2.00 | 0.00 | 0.03 |

The percent recoveries of chylomicrons by optical densitometry for sera "F", "G", "I" and "S" were as follows: 12%, 27%, 20% and 21% respectively. A portion of this percent recovery includes nonspecific background optical density.

It can be readily determined from these data that the porous silica, as used in the present invention, is highly selective for HDL and is, therefore, quite useful in a system for separating HDL from serum containing low and very low density lipoproteins.

Porous silicas suitable for use in the present invention include, in the order of their decreasing effectiveness for selective adsorbtion of HDL:

1) Vydac 101TP - Separations Group, Hesperia, Calif.
2) Crossfield Sorbsil C500 40/60.
3) Regis Chemical Co. 023001; 300 Å/3 $\mu$ silica.
4) E. M. Merck Lichosphere Si 300; 300 Å pore silica.
5) E. M. Merck Fractosil 500; 420–490 Å pore silica.
6) E. M. Merck Fractosil 200; 200 Å pore silica.
7) E. M. Merck Fractosil 1000; 1000 Å pore silica.
8) E. M. Merck Licrosorb Si 100; 100 Å pore silica.
9) Whatman Partisil 5; 5 $\mu$/66—88 Å pore silica.
10) Regis Chemical Co. 024000; 100 Å pore silica.

What is claimed is:

1. A method of selectively separating high density lipoprotein (HDL) from a blood sample containing HDL, LDL, VLDL and chylomicrons which method comprises contacting said sample with finely divided, particulate, porous silica or silicate having a particle size of from about 1 $\mu$ to 1000 $\mu$ in the longest dimension and surface pores of from about 80 Å to 1000 Å in size as absorbant particles to form a complex between the silica or silicate and the HDL and separating said complex from the blood sample by solid/liquid separatory techniques to thereby provide a blood sample substantially free of HDL.

2. The method of claim 1 wherein the absorbant particles are from 2 $\mu$ to 500 $\mu$ in their longest dimension and the pores are from 300 Å to 500 Å in size.

3. The method of claim 1 wherein the absorbant material is microporous silica, silica gel or controlled pore glass.

4. The method of claim 1 wherein the blood sample is further treated with a second reagent system having affinity for very low density lipoproteins (VLDL) and chylomicrons to thereby remove these substances from the blood sample and provide blood which can be analyzed for low density lipoproteins or low density lipoprotein cholesterol without interference from HDL, VLDL or chylomicrons.

5. The method of claim 4 wherein the second reagent system comprises a polyanion and a divalent cation.

6. The method of claim 5 wherein the polyanion is heparin and the cation is $Mn^{++}$.

7. The method of claim 5 wherein the polyanion is dextran sulfate and the cation is $Mg^{++}$.

8. A method as in one of claims 1–7 wherein there is added the step of determining the LDL cholesterol concentration in the blood sample.

9. A method for separating high density lipoproteins from a blood sample while leaving low density lipoproteins suspended therein, which method comprises:

a) providing a compressible chamber having at least one opening in the upper side thereof which is closed by a filter whose pores are of a size which will retain complexes formed between high density lipoprotein in the blood sample and porous silica or silicate particles having a particle size from about 1 $\mu$ to 1000 $\mu$ in the longest dimension and surface pores from about 80 Å to 1000 Å in size as an absorbant material for the high density lipoprotein;

b) combining the blood sample with silica gel particles in the compressible chamber to thereby form a silica gel/high density lipoprotein complex;

c) compressing the compressible chamber to force the blood containing uncomplexed low density lipoprotein through the filter to thereby separate the blood bearing uncomplexed low density lipoprotein from the complexed high density lipoprotein.

10. The method of claim 9 wherein the absorbant particles are from 2 to 500 $\mu$ in their longest dimension and the pores are from 300 to 500 Å in size.

11. The method of claim 10 wherein the absorbant material is microporous silica, silica gel or controlled pore glass.

12. The method of claim 9 wherein there is also added to the compressible chamber a second reagent system having affinity for very low density lipoproteins and chylomicrons to thereby remove these substances from the blood sample and provide blood which can be analyzed for low density lipoproteins without interference from HDL, VLDL or chylomicrons.

13. The method of claim 12 wherein the second reagent system comprises a polyanion and a divalent cation.

14. The method of claim 13 wherein the polyanion is heparin and the cation is $Mn^{++}$.

15. The method of claim 14 wherein the polyanion is dextran sulfate and the cation is $Mg^{++}$.

* * * * *